United States Patent [19]
Yamaguchi et al.

[11] 3,943,574
[45] Mar. 16, 1976

[54] SKI-MASK

[76] Inventors: Takeshi Yamaguchi, 2603, Ogawa-Higashi-cho, Kodaira, Tokyo; Koichiro Imai, 2-6-9, Kokubu-cho, Ichikawa, Chiba, both of Japan

[22] Filed: Sept. 27, 1974

[21] Appl. No.: 509,841

[30] Foreign Application Priority Data
Oct. 5, 1973 Japan.................. 48-116123[U]
Oct. 5, 1973 Japan.................. 48-116124[U]

[52] U.S. Cl................................................... 2/9; 2/209
[51] Int. Cl.².............................................. A41D 13/00
[58] Field of Search............................. 2/9, 8, 10, 209

[56] References Cited
UNITED STATES PATENTS
| | | | |
|---|---|---|---|
| 2,780,814 | 2/1957 | Radnofsky | 2/8 |
| 3,772,707 | 11/1973 | Alosi et al. | 2/9 |
| 3,795,014 | 3/1974 | Simpson et al. | 2/209 |

FOREIGN PATENTS OR APPLICATIONS
| | | | |
|---|---|---|---|
| 460,229 | 5/1928 | Germany | 2/9 |

*Primary Examiner*—Werner H. Schroeder
*Assistant Examiner*—Peter Nerbun
*Attorney, Agent, or Firm*—Woodhams, Blanchard and Flynn

[57] ABSTRACT

A face mask, particularly a ski-mask, comprising a transparent mask body with an interceptive function against the ultraviolet rays and formed to have a curved surface spaced from the skier's face, a pair of ear protectors formed in a bowl-like shape for convenience in covering the ears of the skier and pivotably supporting both side ridge portions of said mask body by the outer side wall thereof, and lock-on members adapted to stop turning round of said mask body relative to said ear protectors and then make it stand still against said ear protector at a desired position, whereby protection of the entire face of the skier, including both of his ears, is ensured from the ultraviolet rays and the cold wind as well as the wind pressure, besides other accidents, and in the meantime delicate adjustment can be achieved for positioning the mask body as required relative to the skier's face.

9 Claims, 13 Drawing Figures

SKI-MASK

BACKGROUND OF THE INVENTION

1. Field of the Invention

The present invention relates to a face mask, particularly a ski-mask, capable of protecting the entire face of the skier including both of his ears, from the ultraviolet rays and the cold wind as well as the wind pressure, besides other accidents during skiing.

2. Description of the Prior Art

As to this kind of ski-mask, there has hitherto been provided a ski-mask wherein a mask body to cover the entire face of the skier is pivotably supported by a band adapted to be set upon the skier's head through the intermediate of the suspension arm attached to the upper edge portion of the mask body (for instance, a ski-mask as disclosed in the Japanese Utility Model Publication No. 32079/1972).

The ski-mask of this kind, however, has some disadvantages such that it necessitates the skier to put on ear protectors separately since it is not provided with any members to protect the ears, and that the mask body cannot be maintained always at a position fully desirable relative to the skier's face, since it is almost impossible to achieve a delicate adjustment with regard to the relative positioning of the mask body against the head band pivotably supporting said mask body.

SUMMARY OF THE INVENTION

An object of the present invention is to provide a ski-mask comprising a transparent mask body with an interceptive function against the ultraviolet rays, which is formed to have a curved surface disposed suitably spaced from the skier's face and which is pivotably supported by the outer side walls of a pair of ear protectors, whereby protection of the entire face of the skier, including both of his ears, is ensured from the ultraviolet rays and the cold wind as well as the wind pressure, besides other accidents.

Another object of the present invention is to provide a ski-mask which is provided with a spongy, flexible and elastic member fixed to the inner side surface of the ear protectors, whereby protection of both ears is ensured from the cold wind and the wind pressure.

A further object of the present invention is to provide a ski-mask characterized in that the upper portion of the peripheral edge of the ear protectors, which are defined in a bowl-like shape opposing the head portion of the skier, is formed to have a suitable space from the head portion of the skier for the purpose to hold therein the lower portion of the skier's cap as well as the arm of the glass spectacles, whereby no trouble is occurred in using both a cap and glasses at the same time.

A still further object of the present invention is to provide a ski-mask, wherein a shaft, which serves as a screw stopper, is penetrates through a perforation defined in the fitting portion of the mask body and then is screwed into a screwed hole provided on the outer side wall of the ear protectors, whereby positioning of the mask body relative to the skier's face can be delicately adjusted as required by fastening said screw stopper.

A still further object of the present invention is to provide a ski-mask, wherein a plurality of engagement depressions are disposed on the outer side wall of the ear protectors along a circle drawn around the center of the journaled portion of the mask body at suitable intervals, while an engaging projection is installed on the inner surface of the fitting portion of said mask body, whereby said engaging projection can selectively get engaged with one of said engagement depressions for achievement of a delicate adjustment in the positioning of the mask body relative to the ear protectors.

DETAILED DESCRIPTION OF THE INVENTION

First, the description will be given with reference to FIGS. 1 and 2 which illustrate a first embodiment of the present invention.

Figure 1:
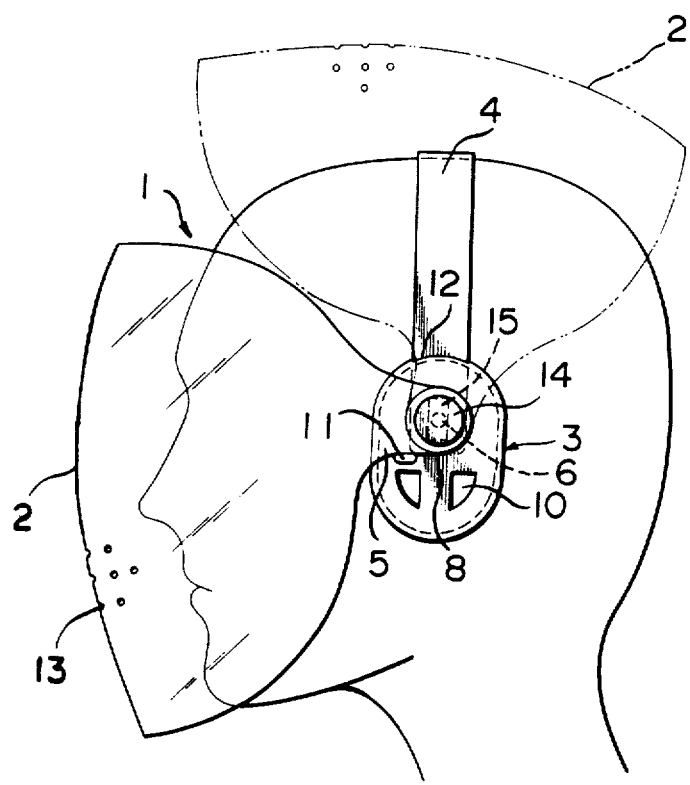
FIG. 1 is a side view of an embodiment of the present invention illustrating how to put it on the head to cover the face therewith.
Figure 2:
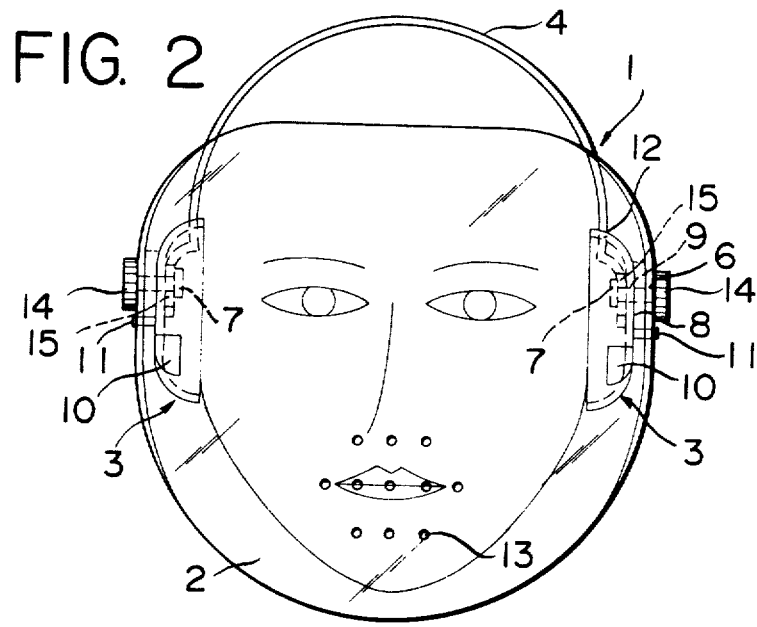
FIG. 2 is a front view of the embodiment shown in FIG. 1.

As shown in FIGS. 1 and 2, a ski-mask 1 comprises: a transparent mask body 2 with an interceptive function against the ultraviolet rays and formed to have a curved surface adapted to be disposed with a suitable space from the skier's face; a pair of ear protectors 3; and a head band 4 to be set onto the skier's head, all of said mask body, said ear protectors and head band are connected together in integration by fastening members consisting of nut member 14 and a bolt 7 penetrates through all of them.

The mask body 2 is made of a synthetic resin material which is comparatively hard, for instance, such as polycarbonate resin, etc., and formed to have a curved surface in such a fashion that it can cover almost the entire portion of the skier's face with a desired space between the face and the surface thereof. The mask body is provided with a fitting portion 5 extending backward from both side edges of the mask body 2, and in this portion there is defined a perforation 6 for insertion of said bolt 7 therethrough.

The mask body 2 is colored either partially or entirely for interception of the ultraviolet rays. In addition, there is no objection if the mask body is of a polarizing glass. This implies that there is not any specific limitation with regard to interceptive means for the ultraviolet rays, whereby various means thus far known are applicable to the present invention.

The ear protector 3, is of a hard synthetic resin material like the mask body, and is formed in a bowl-like shape big enough to cover the entire ear. In the outer wall portion of the ear protector a little upwardly from the center thereof, there is defined a perforation 9 for penetration of the bolt therethrough, while a hole 10 for air ventilation is defined in the lower portion of the ear protector 3.

Further, the ear protector is provided with a stop 11 projectingly installed at a suitable position within an area along which the fitting portion 5 of the mask body turns around for the purpose of catching and holding the lower side edge of the fitting portion 5 of the mask body 2. To be precise, when the mask body 2 is in a position wherein it is disposed in front of the skier's face, the lower edge of the fitting portion 5 of the mask body 2 is restrained by the stop 11 to prevent the body 2 from turning further downwardly.

The head band 4 has an elasticity so as to push both ear protectors toward the ears of the skier respectively, and passing through a elongated hole 12 defined on the side wall of the ear protector 3, each end portion of the head band 4 is introduced into the inner side of the ear protector 3 so as to be fixedly secured to the inside wall of the ear protector by means of the bolt 7.

The numerical reference 13 denotes a plurality of ventilation holes provided in the portion of the mask body corresponding with the position of the mouth and nose of the skier.

Next, in reference to FIGS. 3 – 8 the description will be made with regard to another embodiment of the present invention.

Figure 4:
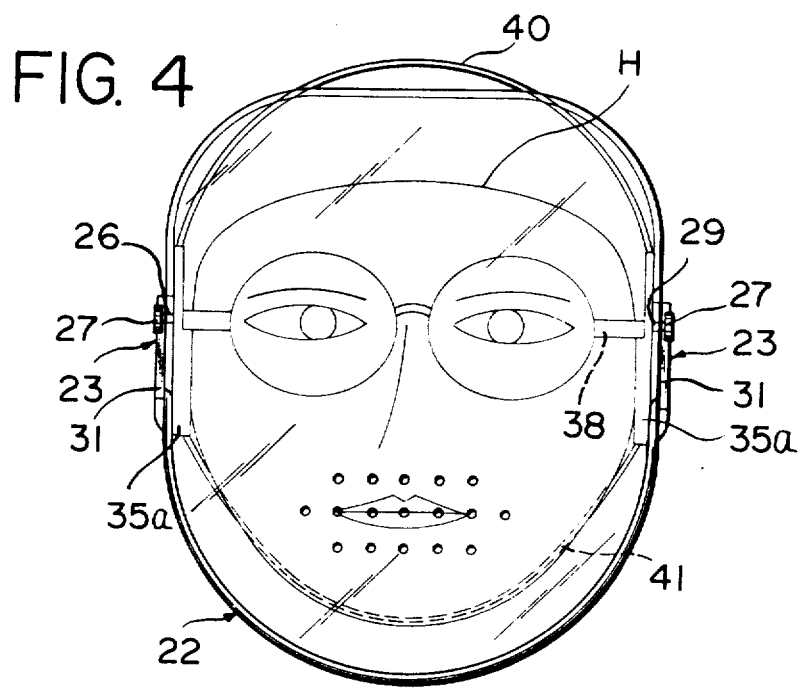
FIG. 4 is a front view of the embodiment shown in FIG. 3.
Figure 3:
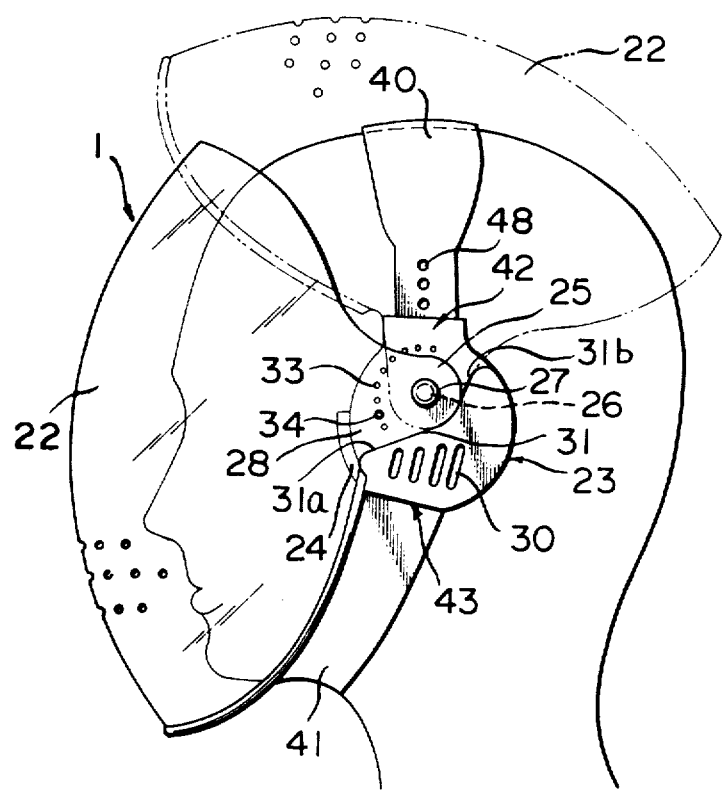
FIG. 3 is a side view of another embodiment of the present invention illustrating how to put it on the head to cover the face therewith.

A mask body 22 shown in FIGS. 3, 4 is substantially identical with what is shown in FIGS. 1 and 2. A shaft-like bar 27, instead of the fastening bolt 7, is inserted through a perforation 26 formed in the fitting portion 25 of the mask body 22 so that the top end portion of said shaft 27 penetrates through a perforation 29 defined in the ear protector 23 so as to be calked in the inner side of the ear protector to effect a pivotable connection between the mask body 22 and the ear protector 23.

The ear protector 23 is of configuration a little different from that shown in FIGS. 1 and 2, as being formed in the shape of a bowl so that it is not as flat as that shown in FIGS. 1 and 2.

In a portion of the outer side wall 28 of the ear protector corresponding with the fitting portion 25 of the mask body 22, there are defined a plurality of engagement depressions 33 in such a fashion that they are disposed along a circle drawn around the center of the perforation 29 with a given radius R, so that a projection 34 provided on the inner side wall of the fitting portion 25 of the mask body 22 can engage with one of the engagement depressions selectively and may release therefrom, if desired.

This structural fashion can be connected in such a fashion wherein fixation is effected by means of the bolt as seen in FIGS. 1 and 2.

On the outer side wall 28 of the ear protector 23, there is further defined a bulged portion to work as a stopping stepped portion 31. One end ridge 31a of the bulged portion engages with the lower edge of the fitting portion 25 of the mask body 22 when the mask body 22 is in front of the skier's face. And then, when the mask body is positioned above the head, as indicated in FIG. 3 by an imaginary line, the other end ridge 31b of the bulged portion engages with the upper edge of the fitting portion 25 of the mask body 22, to restrain the mask body from turning round further upwardly relative to the ear protectors.

The numerical reference 30 denotes a ventilation hole for air.

Figure 6:
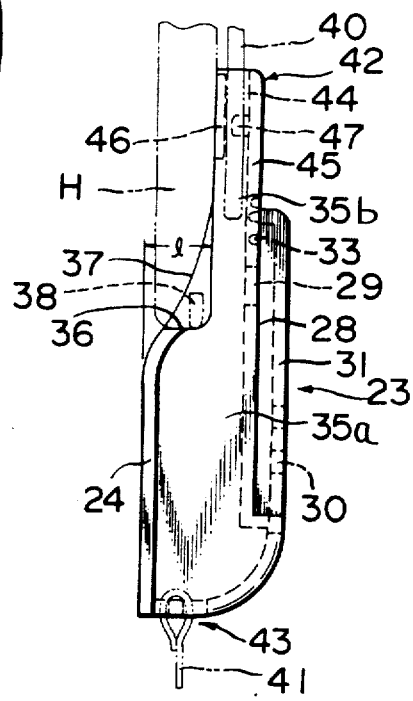
FIG. 6 is a left-side view of the ear protector shown in FIG. 5.

As clearly seen in FIG. 6, the peripheral edge portion of the ear protector 23 facing directly the skier's head is projectingly formed from the outer side wall portion 28 in such a fashion that the upper portion 35b of the peripheral edge projects from the level of the outer side wall a smaller extent than the lower portion 35a thereof, whereby there is defined a space to be measured by $l$ between the upper portion of the peripheral edge of the ear protectors and the side of skier's head, in case the ear protectors are fitted to the ears.

Said space is intentionally formed to hold therein the lower portion of the wearing cap of the skier. Just on the front side of the ear, the lower portion 35a of the projecting peripheral edge runs in a line with the upper portion 35b of the projecting peripheral edge with interposition of a horizontally stepped portion 36, while, on the back side of the ear, the lower portion 35a of the projecting peripheral edge runs in a line with the upper portion 35b of the projecting peripheral edge with interposition of a smoothly curved surface 37.

The space just above the horizontally stepped portion 36 is to provide a room for the arms of glass spectacles of the skier.

The numerical reference 24 denotes a rib to be brought in close contact with the skier's cheek.

Figure 5:
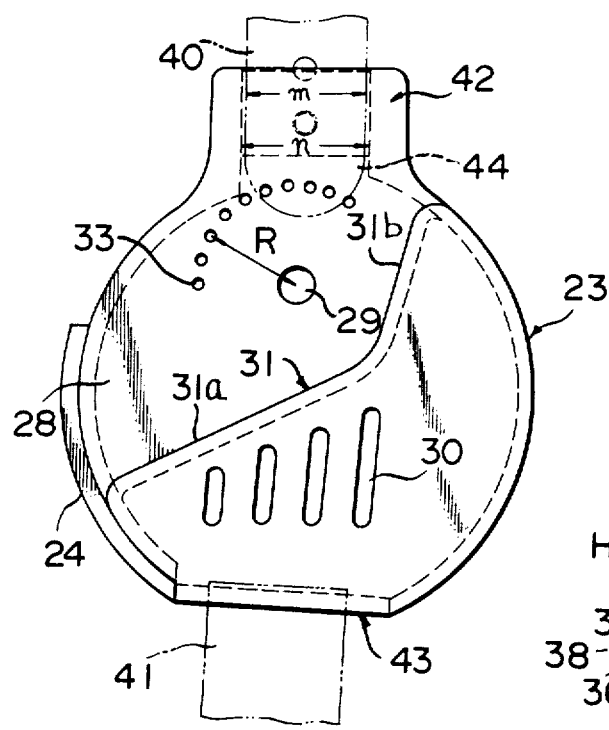
FIG. 5 is a plan view of an ear protector included in the embodiment shown in FIG. 3.

As shown in FIGS. 5 and 6, both in the upper most and the lower most portion of peripheral edge wall of the ear protector 23, there is formed attachment means 42, 43 to which the end portions of a head band 40 or a strap 41 are fixedly secured.

As to the attachment means 42, within this means there is provided an insertion slot 44 for the head band, which is of such a fashion that a projection 47 is installed on the inner side of wall 45 which wall 45 is spaced outwardly from the inner side wall 46.

As to attachment means 43, a pair of elongated holes disposed in parallel with each other serve as an attachment means and the end portion of the strap 41 is led therethrough to make a hoop for fixation to the attachment means.

Figure 7:
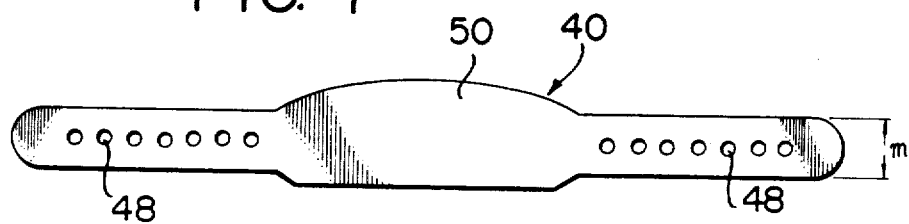
FIG. 7 is a plan view of the head band included in the embodiment shown in FIG. 3.

The head band 40 is made of an elastic material, as indicated in FIG. 7, and formed to have the width $m$ slightly less than the width $n$ of said insertion slot 44 for the head band, and the thickness less than the depth of the insertion slot 44 but larger than the space between the foremost top end of said projection 47 and the inner side wall 46. Further, said head band 40 is formed wider in its middle portion 50 and is provided with a plurality of holes 48 aligned in the lengthwise direction at fixed intervals in both end portions thereof. Said hole 48 has an internal diameter slightly larger than the external diameter of said projection 47.

Figure 8A:
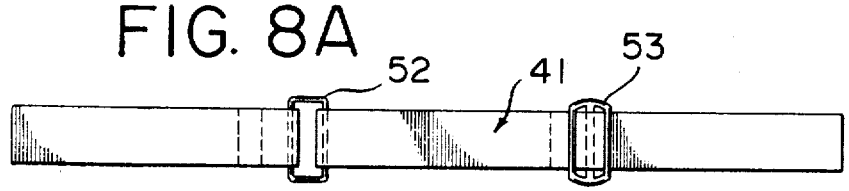
FIG. 8A is a plan view of a chin strap included in the embodiment shown in FIG. 3.
Figure 8B:
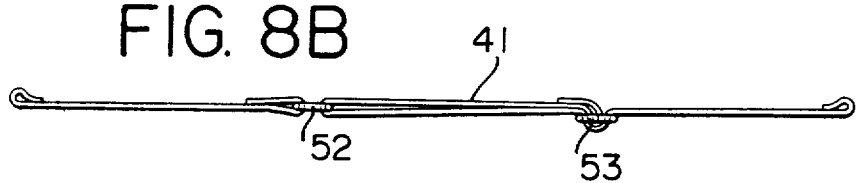
FIG. 8B is a side view thereof.

The strap 41 is formed in a popular structural fashion, as shown in FIG. 8 and both end portions thereof are set up to said attachment means 43 for fixation thereto, as seen in FIG. 6. Further, a ring 52 and a metal fitting 53 are interposed in the middle of said strap 41 for the purpose to adjust the length thereof by changing the position of the latter relative to the former.

Now, a further description will be given hereinunder with regard to a still another embodiment of the present invention shown in FIGS. 9 – 12.

This embodiment comprises a mask body 62, a pair of ear protectors 63, and a head band 80, all of which are combined with each other in a manner wherein a bolt 67 is inserted through an elongated hole 81 of the head band 80, a perforation 69 of the ear protector 63 and a perforation 66 of the mask body 62 and then fastened by means of a nut member 73 interposing a suitable washer 72 therebetween.

The mask body 62 is substantially of identical structure with those of the foregoing embodiments, shown in FIGS. 1 - 4, except that the peripheral edge thereof is fringed with a fringing member 58.

The ear protector 63 is formed after the shape of the bowl with shallower depth than that of the ear protector shown in FIGS. 1 -4. On the outer side wall 68 of the ear protector, there is defined a bulged portion with provision of a stepped-portion 71 to serve as a stop.

When the mask body 62 is disposed in front of the skier's face, said stepped portion 71 engages with the fitting portion of the mask body 62 to prevent the mask body from turning round further downwardly.

The head band 80 is made of a hard material with a sufficient elastic force to push the ear protectors against the skier's ears, and both end portions thereof, wherein an elongated hole 81 is provided, are positioned within a guide groove 84 formed in the upper portion of the inner side wall of the ear protector 63.

Onto the inner side wall of the ear protector 63, there is disposed a spongy elastic member 90 which is fixed to the peripheral edge of the ear protector by adhesives.

The elucidation shall be omitted with regard to other structural matters in this embodiment, because they are just the same as the foregoing ones shown in FIGS. 1 - 4.

OPERATION

Now, the description will be made regarding the first embodiment of the present invention shown in FIGS. 1 and 2.

When the ski-mask 1 is intended to be put on the skier's head, firstly both ear protectors should be pulled outwardly to widen the spacing therebetween so as to be set on both of the skier's ears, taking advantage of the elasticity of the head band 4. And then head band 4 should be positioned over the skier's head. Further, when it is intended for the mask body to change its position relative to the skier's face, a nut member 14 should be loosened so as to turn the mask body 2 around the center of the bolt 7 and then it should be again fastened when the mask body comes just to a position desired.

On this occasion, the mask body can be fixed at whatever position desired between a position wherein it is in front of the face as indicated by a full line in FIG. 1 and a position as indicated by an imaginary line also in FIG. 1.

In addition, the head band 4 can be adjusted in length within limitation allowed by the length of said elongated hole 15 of the head band when the nut member 14 is loosened for this purpose.

Even when the skier puts on a ski-mask, he can hear any sound coming from the outside with the aid of the hole 10. If he intends to take off the mask, he may remove the ear protectors from his ears easily only by pulling thereof outwardly by his hands.

Next, the description will be made regarding a second embodiment of the present invention shown in FIGS. 3 to 8.

In order to put on the ski-mask 1, both ear protectors 23 should be pulled outwardly to widen the spacing therebetween, as mentioned in the foregoing description, so as to be set up on the ears, and then the strap 41 should be applied to his chin.

When the skier wears a cap, the ear protectors are set up to the skier's ears in such a manner that the upper portion 35b of the peripheral edge of the ear protector holds the lower portion of the cap within the space between the upper portion of the ear protector and the skier's head.

Further, when a pair of spectacles is used by the skier, the ear protector 23 should be set up to the ears in such a manner that the arms of the spectacles are kept within the space defined immediately above the horizontally stepped portion 36 of the ear protector 23.

Then the mask body 22 is turned downward around the center of the shaft 27 until the fitting portion 25 of the mask body comes in contact with the stepped portion 31a of the ear protector 23, so that the mask body 22 can stay in a position wherein it is in front of the skier's face to cover almost the entire portion thereof.

When it is intended to change the position of the mask body relative to the face, the mask body should be turned around in the desired direction by applying only a slight force thereto, and then the projection 34 installed on the inner side wall of the fitting portion 25 of the mask body 22 engages with one of the engagement depressions 33 defined on the outer side wall of the ear protector 23. Thereby, the mask body 22 can be placed in any position between the position indicated by a full line in FIG. 3 and the position indicated by an imaginary line also in FIG. 3, by being locked up to one of the engagement depressions 33.

When the mask body 22 is turned around upwardly so far to a position as indicated by an imaginary line in FIG. 3, the fitting portion 25 of the mask body 22 contacts the stepped portion 31b of the ear protector 23.

Adjustment of the head band 40 with regard to the available length thereof can be achieved in such a manner that the head band 40 is released from the stopper projection 47 provided within the insertion slot 44 by pulling or pushing the band to effect movement thereof within the insertion slot 44 so as to achieve the engagement of a desired hole 48 with the projection 47.

Once the head band 40 is put on the skier's head, the thickness of the cap, etc., causes the head band to extend in the outwardly slanting direction from the attachment means 42 of the ear protector 23 so as to tighten engagement between the band and the projection 47 without any occurance of disengagement therebetween.

As to the length of the strap 41, adjustment can be achieved good enough only by moving the metal fitting relative to the ring 52.

Finally, the description will be made regarding a third embodiment of the present invention shown in FIGS. 9 - 12.

In order to put the ski-mask 1 on the skier's head, both ear protectors 63 should be pulled outwardly to widen the spacing therebetween against the elastic force of the head band 80 and then set up onto the ears. In the meantime, the spongy elastic member 90 of the ear protector is pushed toward the skier's ears by the elastic force of the head band 80.

Figure 9:
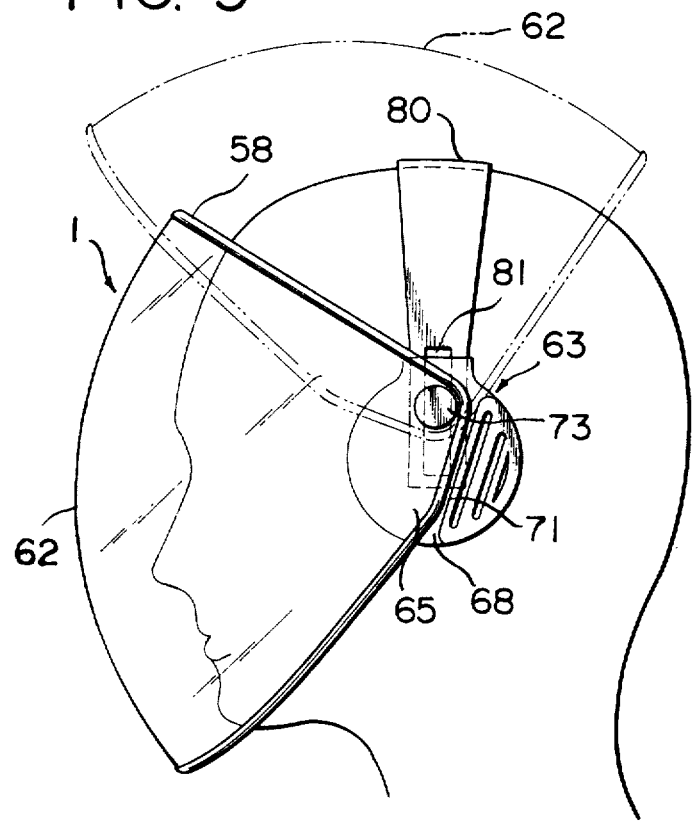
FIG. 9 is a side view of a further embodiment of the present invention illustrating how to put it on the head to cover the face therewith.
Figure 10:
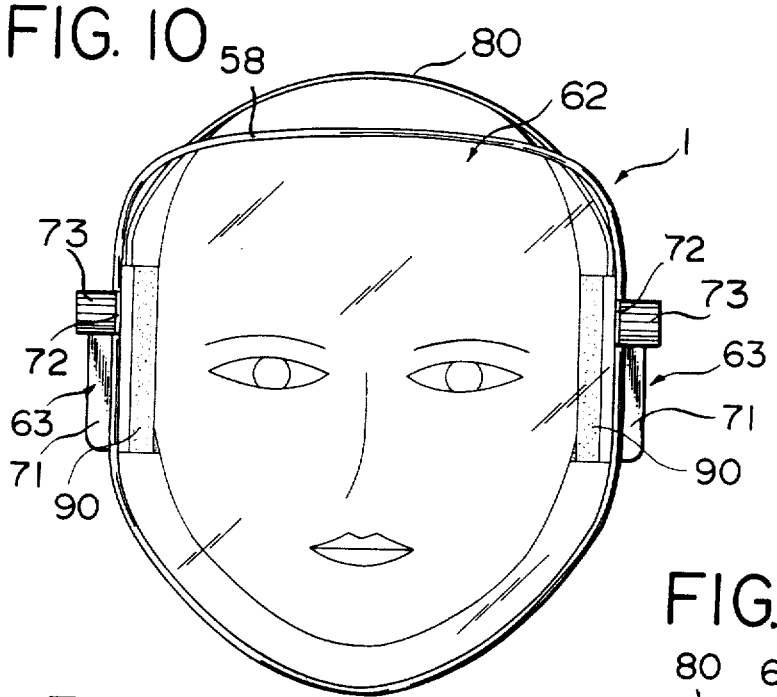
FIG. 10 is a front view of the embodiment shown in FIG. 9.
Figure 11:
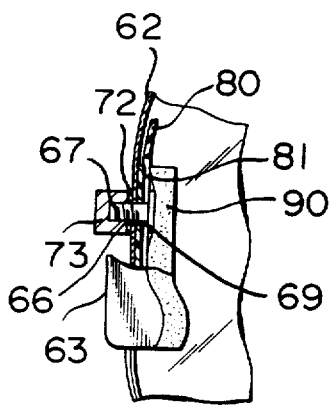
FIG. 11 is a partially cut away sectional view of the principal part of the embodiment shown in FIG. 9.
Figure 12:
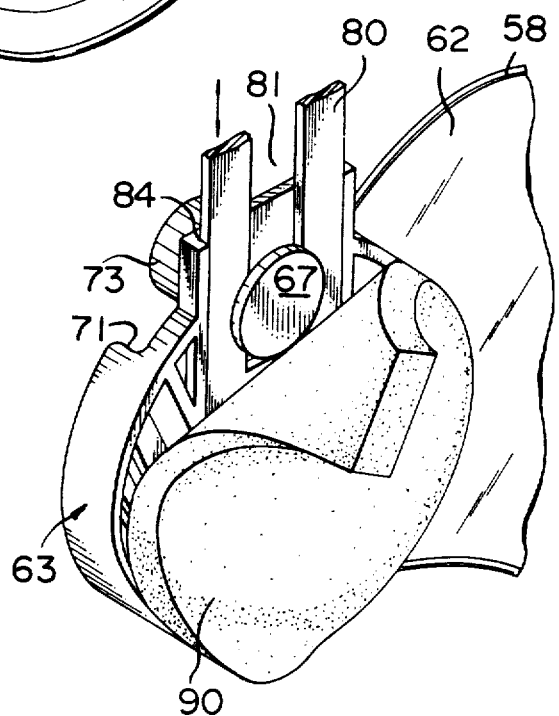
FIG. 12 is a perspective view of the principal part of the ear protector of the embodiment shown in FIG. 9.

When change of the position of the mask body 62 and adjustment of the available length of the head band 80 are required, the nut member 73 should be loosened, whereby the mask body 62 can be turned around the center of the bolt 67 within the range from the position indicated by a full line in FIG. 9 to the position indicated by an imaginary line also in FIG. 9. The head band 80 can freely slide up and down along the guide groove 84 to travel the distance limited by the length of the elongated hole 81, and then the nut member 73 should be fastened after completion of changing the position of the mask body as well as adjustment of the length of the head band 80, as required, within the limitation as above-mentioned.

What is claimed is:

1. A face shield, particularly for a skier, comprising:
   a transparent mask body having a curved surface adapted to be disposed in front of and spaced from a person's face, said mask body having a pair of fitting portions extending from the opposite sides thereof;
   a pair of ear protectors formed of a bowl-like shape for covering the ears of a person, each of said ear protectors being positioned adjacent one of said fitting portions;
   an elongated head band adapted to extend over and engage the person's head for supporting the face shield, the head band having opposite end portions terminating at and engaged with the ear protectors; and
   a pair of connecting means for interconnecting each fitting portion to the adjacent ear protector and the adjacent end portion of the head band;
   said connecting means including first means for permitting swinging movement of the mask body relative to the ear protector so that the mask body can be swingably moved by the person into a selected position relative to the person's head, said connecting means also including second means coacting with said first means for fixedly interconnecting said mask body to said ear protectors in said selected position;
   said connecting means further including third means coacting between the end portion of the head band and the adjacent ear protector for longitudinally adjusting the position of the head band relative to the ear protector to thereby adjust the band so that it is able to accommodate different head sizes.

2. A face shield according to claim 1, wherein said head band is of a U-shaped configuration and is formed from a stiff, resilient material so that the ear protectors, which are mounted adjacent the free ends of the U-shaped configuration, will be resiliently urged into snug engagement with the person's head.

3. A face shield according to claim 1, wherein said first means comprises a shaft portion which extends between and interconnects the fitting portion and the adjacent ear protector and the adjacent end portion of the head band, said second means comprising a threaded fastener supported on said shaft portion, and said third means comprising an elongated slot formed in the end portion of the head band and extending longitudinally thereof, said shaft portion projecting through said slot, whereby loosening of the threaded fastener relative to the shaft portion permits the mask body to be angularly moved relative to the ear protectors and additionally permits the head band to be adjusted relative to the ear protectors, and whereby tightening of the threaded fastener relative to shaft portion both fixes the mask relative to the ear protectors and also fixes the head band relative to the ear protectors.

4. A face shield according to claim 3, wherein said shaft portion comprises a bolt which projects through the slot in the head band and also projects through aligned openings formed in the ear protector and the fitting portion, the head of said bolt being positioned within the ear protector, and the threaded fastener comprising a nut member threadably engaged on the outer end of the bolt so as to be positioned externally for access by the person.

5. A face shield according to claim 1, wherein each ear protector has a stop fixed thereto and projecting outwardly therefrom, said stop being adapted for engagement with the mask body for limiting the downward swinging movement of the mask body and thereby maintain the mask body in a position wherein it is normally disposed in front of the person's face.

6. A face shield according to claim 5, wherein a spongy, flexible, elastic member is fitted on the inner side of each ear protector for cushioning the engagement of the ear protector against the person's head.

7. A face shield according to claim 1, wherein the ear protector has an upper peripheral edge portion which is positioned adjacent but slightly spaced from the person's head when the ear protector is in engagement with the person's head, whereby a cap worn by the person can extend into the space between the person's head and the upper peripheral portion.

8. A face shield according to claim 1, wherein the first means includes a shaft portion joining the ear protector and the fitting portion and defining a pivot axis for the mask body, and the second means including a plurality of depressions defined on the outer surface of the ear protector along a circle drawn about the pivot axis and a projection mounted on the inner surface of the fitting portion and disposed for engagement within a selected one of the depressions.

9. A face mask, particularly for use by a skier, comprising:
   a transparent mask body adapted to be disposed in front of and spaced from a person's face, the mask body having a pair of fitting portions extending rearwardly from the sides thereof;
   a pair of cup-shaped ear protectors for covering the ears of the person, each ear protector being disposed adjacent and interconnected to one of the fitting portions associated with the mask body;
   connecting means coacting between each fitting portion and the adjacent ear protector for interconnecting same, said connecting means including a shaft portion extending between the fitting portion and the respective ear protector for permitting swinging movement of the mask body relative to the ear protectors to thereby selectively adjust the position of the mask body relative to the person's face, said connecting means also including a locking device for fixedly securing the mask body relative to the ear protectors at a desired position; and
   a U-shaped head band extending between and having the opposite ends thereof fixedly connected to said pair of ear protectors, said head band being of a stiff but resilient material for resiliently urging the ear protectors inwardly toward one another so that they snugly engage the opposite sides of the person's head, whereby said head band and said ear protectors solely support the face mask on the person's head.

* * * * *